United States Patent [19]

Taylor

[11] Patent Number: 4,881,551
[45] Date of Patent: Nov. 21, 1989

[54] SOFT TISSUE CORE BIOPSY INSTRUMENT
[75] Inventor: Glenn N. Taylor, Longmont, Colo.
[73] Assignee: Hart Enterprises, Inc., Wyoming, Mich.
[21] Appl. No.: 150,984
[22] Filed: Feb. 1, 1988
[51] Int. Cl.4 .............................................. A61B 10/00
[52] U.S. Cl. ..................................... 128/754; 128/305
[58] Field of Search ............... 128/305, 310, 749, 751, 128/752, 753, 754

[56] References Cited
U.S. PATENT DOCUMENTS 4,600,014  7/1986  Beraha ................................. 128/754
4,699,154  10/1987  Lindgren ............................ 128/754
4,776,346  10/1988  Beraha et al. ....................... 128/754

FOREIGN PATENT DOCUMENTS 0010321  4/1980  European Pat. Off. ............ 128/754
8701097  11/1987  World Int. Prop. O. .......... 128/754

Primary Examiner—Max Hindenburg
Assistant Examiner—Randy Citrin
Attorney, Agent, or Firm—Thomas R. Vigil

[57] ABSTRACT

The soft tissue core biopsy instrument comprises a proximal outer barrel member having a distal end and a proximal end; a distal inner barrel member which is slidably received within said outer barrel member, which has a distal end and a proximal end and which has a stop in said distal end; a cannula driver in said inner barrel member; a cannula extending distally from said inner barrel member, being fixed to said cannula driver, and having a distal tip, said cannula driver being slidably received in and movable within said inner barrel member and said cannula extending a predetermined distance out of a distal end of said inner barrel member when the instrument is in an at-rest condition; a stylet having a distal end, a proximal end, and being removably received in said outer barrel, in said inner barrel, and in said cannula, said distal end having a biopsy sample receiving notch therein; a stylet hub mounted to said proximal end of said stylet; said stylet hub being removably attached to the proximal end of said proximal outer barrel member to enable multiple biposies to be obtained with one insertion of said cannula, said stylet extending distally from said hub and within said cannula and having a distal tip portion (a) positioned within said cannula when the instrument is in an at-rest position and (b) extending distally of said distal tip of said cannula in position to capture a biopsy sample when the instrument is in a cocked condition; biasing means within said inner barrel member between said stop and said cannula driver for biasing said cannula driver; latching means associated with said cannula driver and said inner barrel member for latching said cannula driver in a proximally retracted cocked position within said outer barrel member and said inner barrel member against the biasing action of said biasing means; and a trigger, associated with said latching means, for unlatching said latching means, said trigger, upon being actuated for unlatching of said latching means, allowing said biasing means to quickly return said cannula driver and said cannula to said distally extending position thereof and over said stylet distal tip portion.

16 Claims, 3 Drawing Sheets

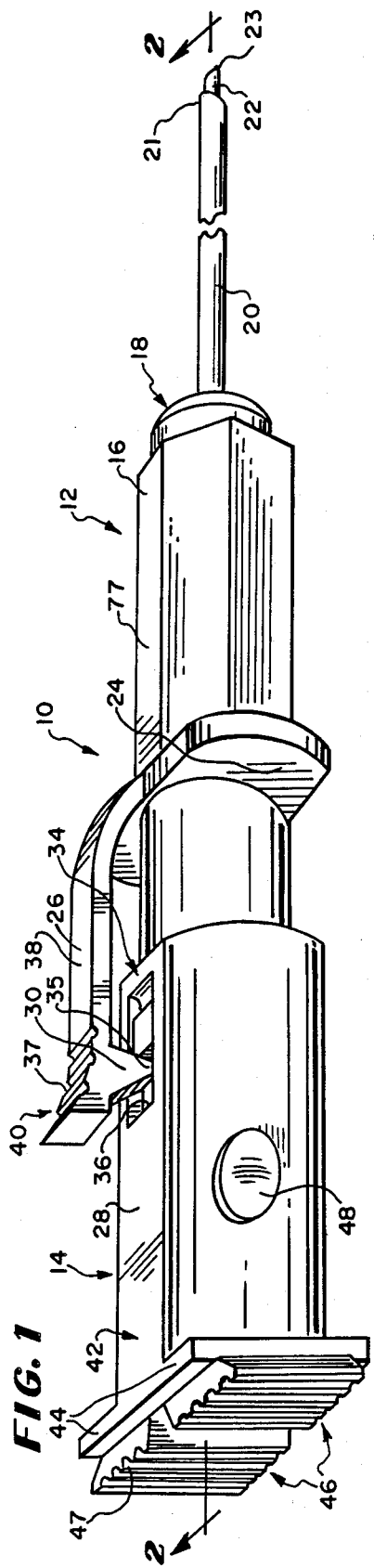
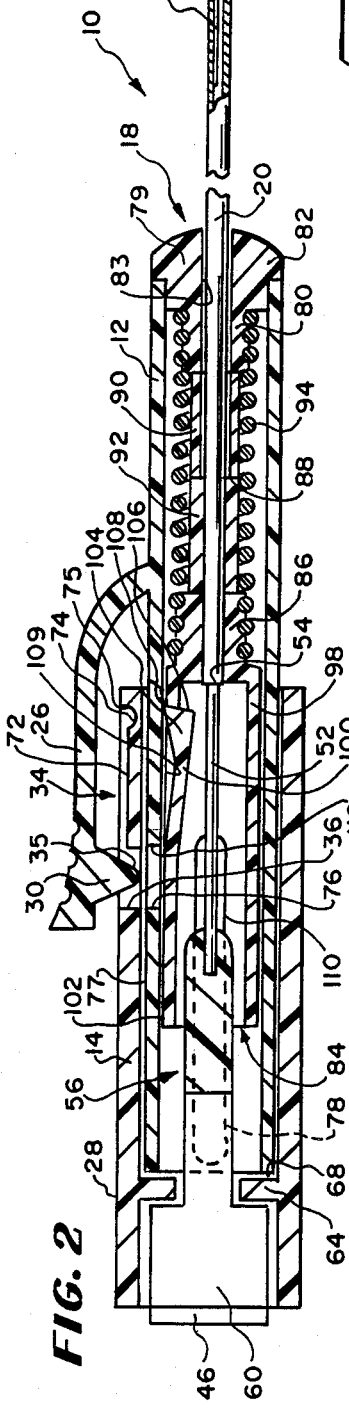
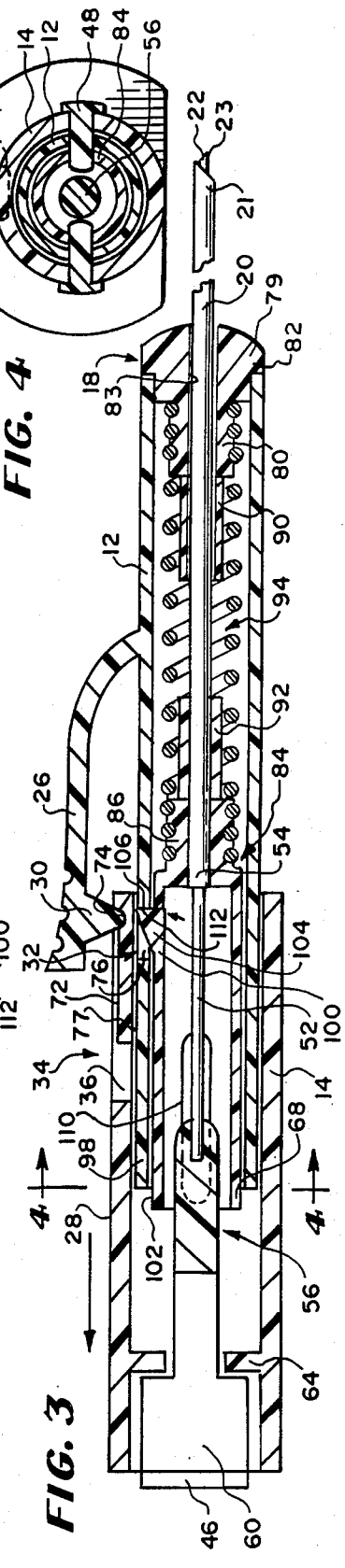
FIG. 1
FIG. 2
FIG. 3
FIG. 4

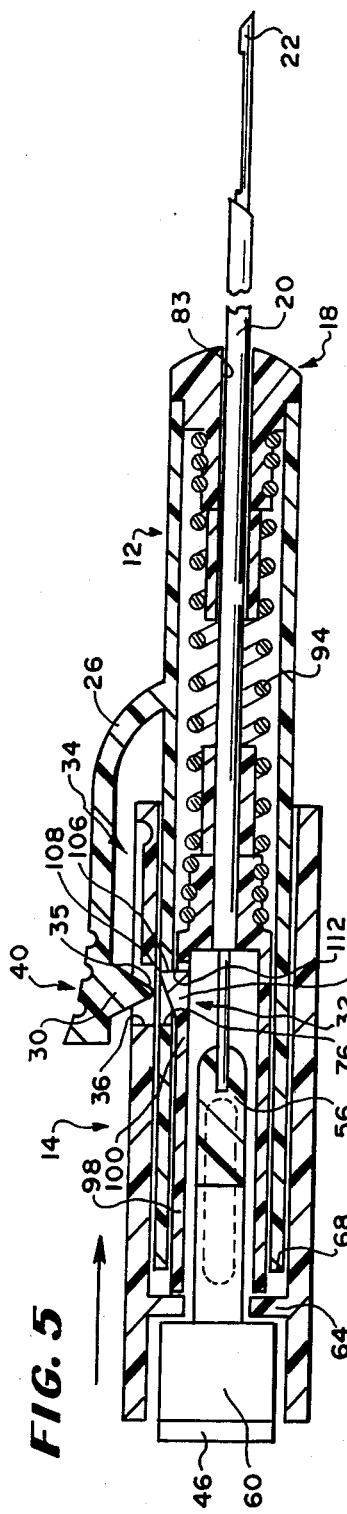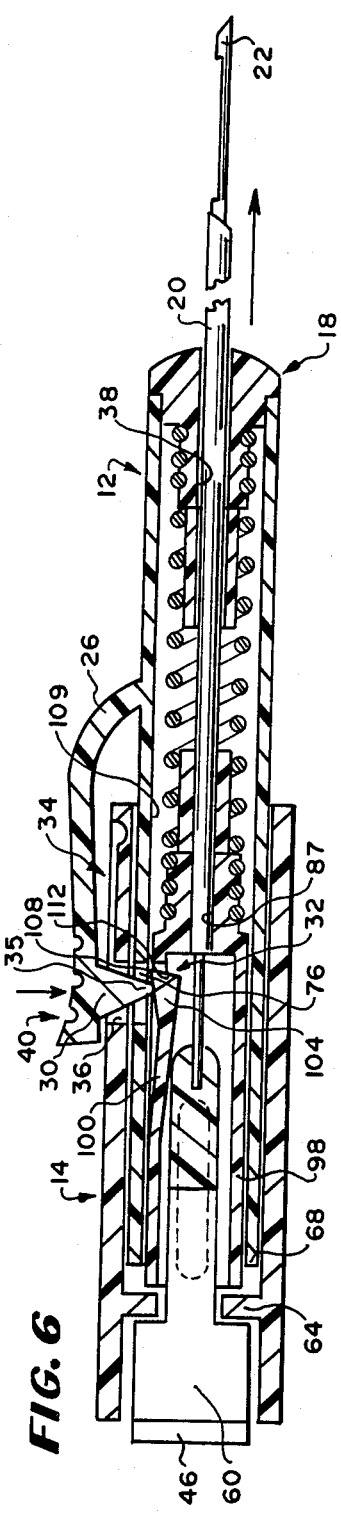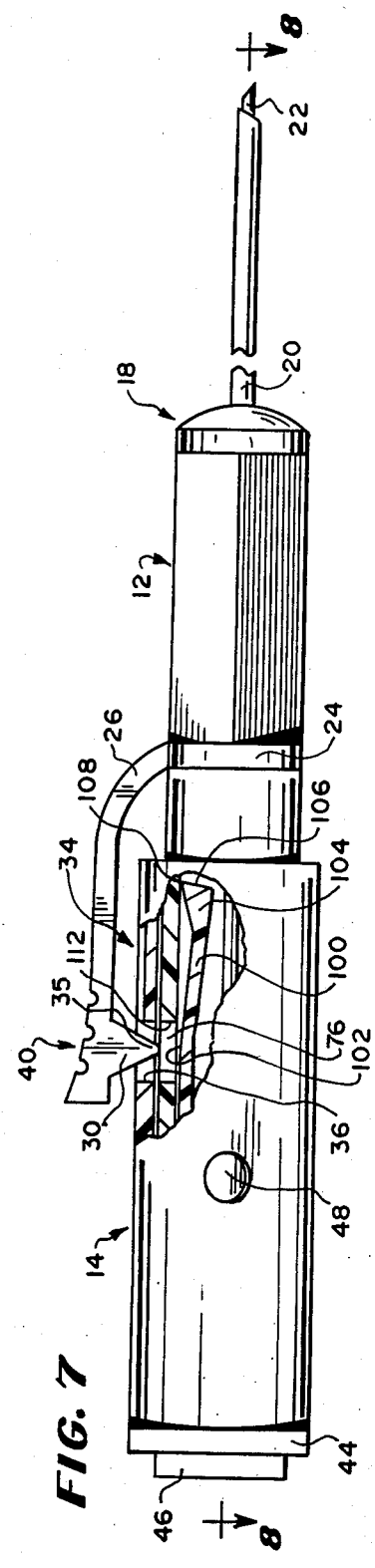

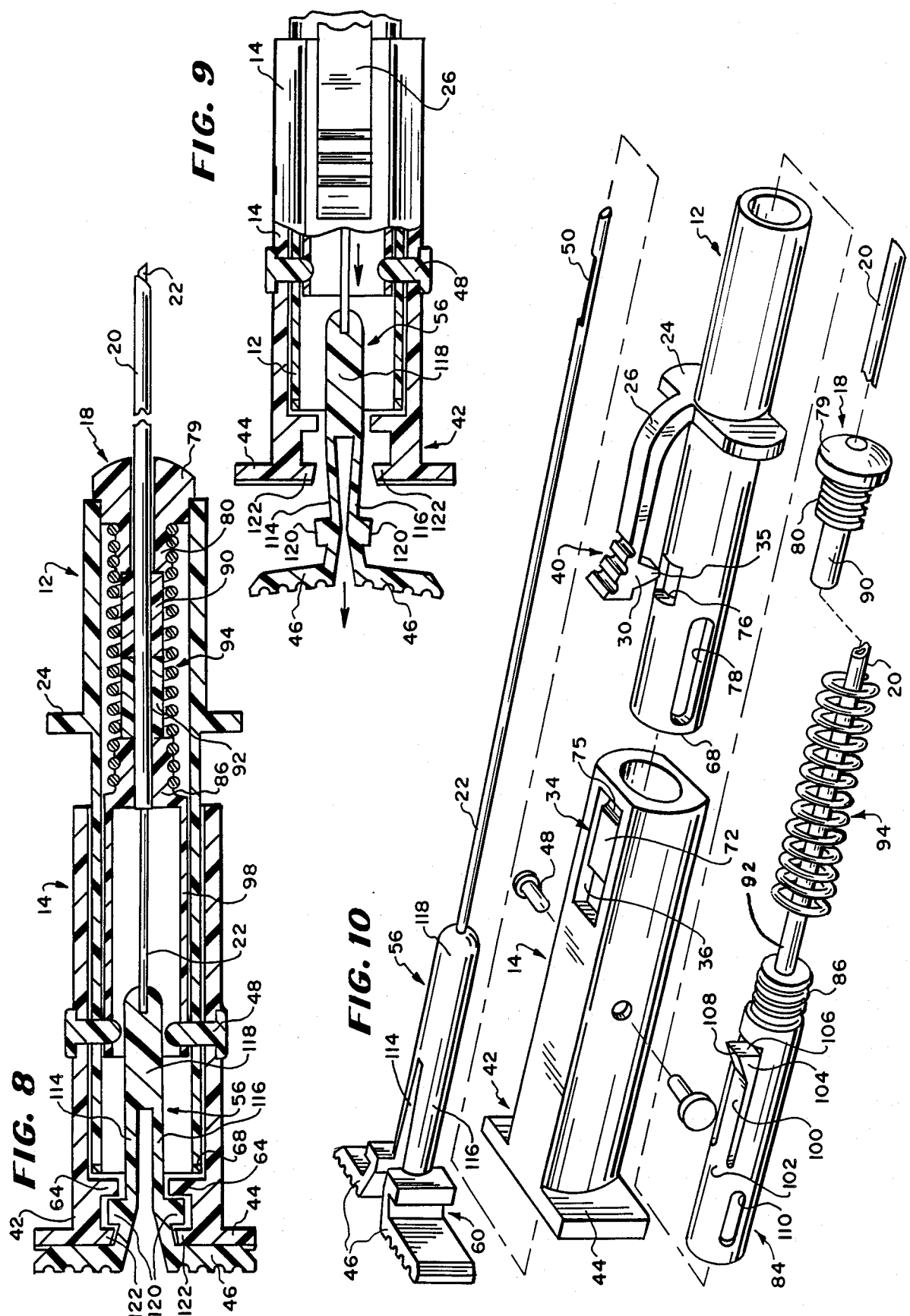

SOFT TISSUE CORE BIOPSY INSTRUMENT

BACKGROUND OF THE INVENTION

1. Field of the Invention

The present invention relates to a soft tissue core biopsy instrument which is semi-automatic in operation. More specifically, the biopsy instrument of the present invention provides an instrument which can be operated using only one hand and which includes a cutting cannula which is caused to move in a snap action over a stylet which is manually advanced.

2. Description of the Prior Art

Heretofore, various soft tissue core biopsy instruments have been proposed.

The most well known instrument used in this procedure is manufactured by Travenol Laboratories of Deerfield, IL and is sold under the mark "TRU-CUT". This instrument enjoys 98% of the existing market. As disclosed in U.S. Pat. No. 3,477,423, the instrument comprises a two piece assembly; an outer cutting cannula mounted to one hub member and an inner stylet with a sampling notch ground into it mounted to a second hub, with the hubs being slidably interlocked. The instrument is assembled and placed into the body with the outer cutting cannula just to the rear of a lancet point or bevelled distal end of the stylet. Upon inserting the device up to or in front of the area to be biopsied, advancement of the assembly is halted. The stylet is manually advanced distally of the cannula with the cannula held stationery. Upon advancement of the stylet, the specimen notch is exposed. Tissue surrounding the stylet contracts into the specimen notch and the cutting cannula is then manually advanced distally over the stylet, slowly shearing off the tissue entrapped in the stylet's specimen notch. The instrument is then either (a) withdrawn and the stylet advanced distally to expose the tissue for preparation for study or (b) left in place and only the stylet is proximally removed from within the cannula so a determination of successful sampling may be made. If the sampling was not successful, the stylet may be reinserted into the cannula, which remains positioned within the patient, and a attempt to reposition the assembly of stylet and cannula and repeat sampling can be made.

Such technique using this basic design of a biopsy instrument is referred to as a manual technique. One drawback to the manual technique is that it requires a great deal of manual dexterity and motor coordination, along with the use of both hands, to advance the stylet while maintaining the position of the cannula and then to maintain the position of the stylet while advancing the cannula.

Another drawback is that the cannula is advanced relatively slowly, resulting in an extremely poor cutting action and allowing the surrounding tissue an opportunity to collapse, thus making no use of the stored kinetic energy in the material being severed.

The Beraha U.S. Pat. No. 4,600,014 discloses a transrectal prostate biopsy device which comprises a handle held in a physician's palm, and a guide tube extending forwardly of the handle. A cannula is slidably disposed within the guide tube and is movable from within the guide tube forwardly out of the distal end of the guide tube. A sampling stylet is telescopically disposed within the cannula and projects from the rear of the handle. A knob is provided at the proximal end of the stylet for extending a distal end of the stylet out of the distal end of the guide tube to expose a sampling thereon. The physician holds the handle in one hand using his index finger at the distal end of the guide tube to guide the instrument to a selected transrectal point on the prostate. Upon locating the point, the one hand holds the instrument steady while the other hand pushes the stylet forward and then pushes the cannula over the stylet to sever the tissue within the sampling slot. The device is then withdrawn to gain access to the sample. In one embodiment of the device, the cannula, when in the retracted position, is spring loaded by means fo a compressed spring. A release lever, which works against the compressed spring can be activated to release compression of the spring which then expands and pushes the cannula outwardly over the stylet.

This instrument, as stated, requires two handed operation. Also, since the stylet is not removable proximally from within the handle, the entire instrument must be withdrawn to obtain access to the sample.

Within the last two years, a fully automatic instrument manufactured by Radiplast, Inc. of Sweden has been introduced and is described in U.S. Pat. No. 4,699,154. This instrument comprises a reusable, spring-loaded box-shaped housing or handpiece, which activates a disposable cannula and stylet set. Both the stylet and cannula are activated in rapid succession.

The instrument has the advantage of eliminating the dexterity and motor coordination necessary in use of manual devices and also eliminates the slow cutting action of the manually advanced cannula and replaced it with a very quick, clean cut. This instrument, however, also has its drawbacks.

First, the reusable handpiece is very large, heavy, cumbersome, and expensive. Its weight and the awkwardness in using same preclude it from being used with imaging equipment other than ultrasound, inasmuch as it must be inserted into the body with the user maintaining control of the handpiece at all times. Thus, the patient cannot be imaged with many conventional radiographic apparatus, such as CAT scanners. A further drawback is encountered in automatically activating both the stylet and the cannula, as opposed to activating the stylet manually, in that the rapid speed at which the cannula follows the stylet into the tissue does not allow much tissue to collapse into the specimen notch, limiting the size of the sample.

Also, it does not allow imaging of the device with the stylet and sampling notch in the actual tissue to be sampled and further, since a handpiece is utilized, the user cannot remove the stylet proximally from within the instrument to inspect the sampling and the entire instrument must be removed to obtain access to the sampling, so that, if a repeat sampling is required, the entire instrument must be reinserted. Also, since the handpiece is reuseable, additional costs above the purchase price are involved in cleaning, maintenance, and maintaining sterility of the handpiece.

The semi-automatic soft tissue core biopsy instrument of the present invention, as will be described in greater detail hereinafter, is completely disposable, lightweight and inexpensive. Further, it allows the user to advance the stylet manually, and then rapidly advance the cutting cannula automatically, all with one hand. Also, since the stylet is removable from the proximal end of the instrument, the position of the cannula within the body need not be disturbed if a repeat biopsy is required.

SUMMARY OF THE INVENTION

According to the invention, there is provided a soft tissue core biopsy instrument comprising: A soft tissue core biopsy instrument comprising: a proximal outer barrel member having a distal end and a proximal end;
- a distal inner barrel member which is slidably received within said outer barrel member, which has a distal end and a proximal end and which has a stop in said distal end;
- a cannula driver in said inner barrel member;
- a cannula extending distally from said inner barrel member, being fixed to said cannula driver, and having a distal tip, said cannula driver being slidably received in and movable within said inner barrel member and said cannula extending a predetermined distance out of a distal end of said inner barrel member when the instrument is in an at-rest condition;
- a stylet having a distal end, a proximal end, and being removably received in said outer barrel, in said inner barrel, and in said cannula, said distal end having a biopsy sample receiving notch therein;
- a stylet hub mounted to said proximal end of said stylet;
- said stylet hub being removably attached to the proximal end of said proximal outer barrel member to enable multiple biopsies to be obtained with one insertion of said cannula, said stylet extending distally from said hub and within said cannula and having a distal tipportion (a) positioned within said cannula when the instrument is in an at-rest position and (b) extending distally of said distal tip of said cannula in position to capture a biopsy sample when the instrument is in a cocked condition;
- biasing means within said inner barrel member between said stop and said cannula driver for biasing said cannula driver;
- latching means associated with said cannula driver and said inner barrel member for latching said cannula driver in a proximally retracted cocked position within said outer barrel member and said inner barrel member against the biasing action of said biasing means;
- and a trigger, associated with said latching means, for unlatching said latching means, said trigger, upon being actuated for unlatching of said latching means, allowing said biasing means to quickly return said cannula driver and said cannula to said distally extending position thereof and over said stylet distal tip portion.

BRIEF DESCRIPTION OF THE DRAWINGS

FIG. 1 is a perspective side view of the biopsy instrument of the present invention in an at-rest condition.

FIG. 2 is a longitudinal cross sectional view through the instrument and is taken along line 2—2 of FIG. 1.

FIG. 3 is a longitudinal cross sectional view similar to FIG. 2 and shows a cannula driver of the instrument being proximally biased.

FIG. 4 is a radial cross sectional view through the instrument and is taken along line 4—4 of FIG. 3.

FIG. 5 is a longitudinal cross sectional view similar to FIGS. 2 and 3 and shows a stylet of the instrument being advanced distally.

FIG. 6 is a longitudinal cross sectional view similar to FIG. 5 and shows a cannula of the instrument being projected distally over the advanced stylet upon actuation of a trigger of the instrument.

FIG. 7 is a perspective side view of the instrument, partly in section, and shows return of the instrument to an at rest condition upon release of the trigger.

FIG. 8 is a longitudinal cross sectional top plan view of the instrument and shows the proximal removable stylet and stylet hub of the instrument.

FIG. 9 is a top plan view, partly in section of a proximal end portion of the instrument and shows the stylet and stylet hub being removed proximally from the instrument.

FIG. 10 is an exploded perspective view of the biopsy instrument of the present invention and their structures forming method of assembly.

DESCRIPTION OF THE PREFERRED EMBODIMENT

Referring now to the drawings in greater detail, there is illustrated in FIG. 1 the semi-automatic soft tissue core biopsy instrument 10 of the present invention.

As illustrated, the instrument 10 is syringe-like and has a distal, inner barrel member 12 and a proximal, outer barrel member 14. At a distal end 16 of inner barrel member 12 is a nose or plug 18. Extending through and distally of the plug 18 is a hollow cannula 20 having a pointed distal end 21 and having a stylet 22, also having a pointed end 23, therein. The pointed ends 21 and 23 are oppositely directed.

The inner barrel member 12 also has two outwardly extending finger flanges 24 approximately centrally along its length, each flange 24 being on an opposite side of the instrument 10. The flanges are formed integrally with the inner barrel member 12.

The inner barrel member 12 further has an integral lever arm 26 extending upwardly therefrom an proximally over an upper surface 28 of the proximal outer barrel member 14. The lever arm 26 originates at a position corresponding to the position of the finger flanges 24 along the length of the barrel member 12 and terminates at a position where a downwardly extending V-shaped trigger element 30 thereof can co-act with latching means 32 as will be described in greater detail hereinafter. Latching indicator means 34 are cut into the top surface 28 of the proximal outer barrel member 14.

The lever arm 26 is formed in such a manner as to be downwardly biased, with a downwardly directed point 35 of the V shaped trigger element 30 resting within a cutout 36 of the latching indicator means 34 when the instrument 10 is in an at-rest condition.

Serrations 37 are provided along a top surface 38 of the arm 26 along a proximal end section 40 of the arm 26.

The outer barrel member 14, incorporating the latching indicator means 34 for the trigger element 30 also has, extending laterally outwardly along a proximal end 42 thereof a rear flange 44 against which a pair of wings 46 rest. The wings 46 are serrated along a proximally facing end face 47 thereof and will be described in greater detail in connection with the description of FIGS. 8 and 9.

At least one, and preferably two, pins 48, are provided for maintaining the various components of the instrument 10 unitary and for maintaining the components against relative rotation. Such rotational position of the components must be maintained to keep the pointed end 21 of the cannula 20 in opposite alignment with the pointed end 23 of the stylet 22, as will be described hereinafter.

Illustrated in FIG. 2 is a longitudinal cross sectional side view through the instrument 10 and shows the position of the various components of the instrument 10, when the instrument 10 is in an at rest condition.

The stylet 22 is now seen to have an upwardly facing sampling notch 50 ground therein at a distal position thereon, just behind the pointed tip 23 thereof. The notch 50, when the instrument 10 is at rest, is located just inside the pointed tip 21 of the cannula 20. A proximal end 52 of the stylet 22 exits a proximal end 54 of the cannula 20 and extends a predetermined distance proximally where it is fixed within a hub 56 for the stylet 22.

The hub 56 is somewhat T shaped and has a proximal end portion 60 which is increased in diameter.

The outer proximal barrel member 14 also has an inwardly extending circumferential rib 64 which limits distal insertion of the hub 56 into the proximal outer barrel member 14 by abutment against the increased in diameter portion 60 of the hub 56. Further, the rib 64 also forms a stop 64 which limits proximal motion of the inner barrel member 12 within the outer barrel member 14 by abutting against a rear or proximal end edge 68 of the inner barrel member 12.

As stated above, the outer barrel member 14 includes the latching indicator means 34 for the trigger element 30 of the instrument 10. The latching indicator means 34 include the cutout 36 which extends through the thickness of outer barrel member 14 at a position along the upper surface 28 such that the point 35 of the trigger element 30 rests within the cutout 36 when the instrument 10 is in an at-rest condition.

Distal to the cutout 36 is a small, reduced in thickness area 72 of upper wall 28 which terminates distally in a groove 74, with a distal end wall 75 of the groove 74 returning to the thickness of the outer barrel member 14. The point 35 of the trigger 30, as will be described hereinafter, can be slid distally and proximally within the latching indicator means 34.

The inner barrel member 12 also has a full thickness cutout 76 in an upper surface 77 thereof which is aligned directly beneath the cutout 36 in the proximal outer barrel member 14 when the instrument 10 is in an at-rest condition.

Further, to provide for limited slidability of the inner barrel member 12 within the outer barrel member 14, even though they are maintained unitary by the pins 48, elongate longitudinal lateral slots 78 (shown in phantom) are provided in the inner barrel member 12 for receiving the pins 48 therein, thus allowing limited relative longitudinal movement between the inner barrel member 12 and the outer barrel member 14.

Turning now to the plug 18 at the distal end 16 of the inner barrel member 12, the plug 18 has a somewhat mushroom shape, a head portion 79 thereof fitting snugly within the barrel member 12 and having a first inwardly stepped proximal portion 80 extending proximally within the barrel member 12. The head portion 79 also has, along its distal end, an outwardly extending flange 82 which has a diameter equal to the diameter of the inner barrel member 12 to provide a smooth slightly rounded distal end 16 to the inner barrel member 12. The plug 18 also has a central longitudinal bore 83 through which the cannula 20 slidably extends.

The inner barrel member 12 further incorporates a slidable, somewhat Y shaped in cross section cannula driver 84. A first inwardly stepped distal end portion 86 of the cannula driver 84, forming part of the tail of the Y, extends distally within the inner barrel member 12. The first stepped end portions 80 and 86 are equal in size and diameter and are threaded. A second inwardly stepped portion 90 extends proximal of stepped end portion 80 of the plug 18 and a second inwardly stepped portion 92 extends distally of stepped end portion 86 of the cannula driver 84. A spring 94 is threadedly fixed, at one end, over and to the first stepped portion 80 of the plug 18 and at its other end over and to the first stepped portion 86 of the cannula driver 84. When the instrument 10 is in an at-rest position, the spring 94, is contracted. The second stepped portions 90 and 92 are loosely received within the remaining central coils of the spring 94 and abut one another, the portions 90 and 92 being maintained in abutting relationship by the contracted spring 94 when the instrument 10 is in an at rest condition. The second stepped portions 90 and 92 serve to limit distal motion of the cannula driver 84 within barrel member 12, as will be described hereinafter.

The cannula driver 84 also has an elongate cylindrical proximally extending body portion 98 which has a diameter almost equal to an inner diameter of the distal inner barrel member 12, providing for slidability of the cannula driver 84 within the inner barrel member 12.

This body portion 98 has a distally terminating flap 100 cut through a precise area of its thickness along an upper surface 102 thereof. The flap 100 has a conically, distally radially outwardly flanged distal end portion 104. The end portion 104 terminates in a thick, vertical distal end wall 106. As shown, when the instrument 10 is in an at rest condition, the end portion 104 of the flap 100 is flexed inwardly into the body portion 98, with a top end edge 108 of the vertical distal end wall 106 bearing against the inner surface 109 of the inner barrel member 12, at a position distal to the position of the cutout 76 in the inner barrel member 12. The necessity for precise positioning of the flap 100 will be further described in connection with the description of FIG. 3, however, here it is to be noted that the groove 74 of the latching indicator means 34 is positioned directly above the distal end portion 104 of the flap 100 when the instrument 10 is in an at rest condition.

The cannula driver 84 is also maintained integral within the instrument 10 by the pins 48 and, since the cannula driver 84 must be limitedly and independently slidable within the inner barrel member 12, lateral elongate longitudinal slots 110 are provided for receiving the pins 48 therein.

In use, the instrument 10 is positioned for taking of a biopsy specimen in such resting condition and the various components of the instrument 10 are then manipulated as will be described below to obtain the biopsy specimen.

Turning now to FIGS. 3–7, the interaction between the various components of the instrument 10, during its use, and in non-resting conditions thereof, is illustrated.

In FIG. 3, as illustrated, once the instrument 10 has been precisely positioned relative to the tissue within a body to be biopsied, a user of the instrument 10, using only one hand, maintains the position of the inner barrel member 12, such as between thumb and forefinger, and pulls rearwardly on the outer barrel member 14 with the other fingers of his hand until the point 35 of the V shaped trigger 30, which has dragged along an upper surface of the reduced in thickness portion 72 of the latching indicator means 34, falls into the groove 74 at the distal end of the latching indicator means 34.

When such position is reached, bearing in mind the positioning of the distal end edge 108 of the flap 100 of the cannula driver 84, relative to the position of the groove 74, the user will hear an audible "click". The "click" is produced by a sudden upward motion of the flap 100 and engagement of the distal end 104 of the flap 100 within the cutout 76 of the inner barrel member 12, with the vertical distal end wall 106 of the flap 100 abutting against a distal end edge 112 of the cutout 76. Upon such engagement between the flap 100 and the inner barrel member 12, the spring 94 is expanded to a significant degree and maintained in such expanded state by the engagement between the flap 100 and the cutout 76. The flap 100 and cutout 76 form the latching means 32 of the instrument 10.

It will be noted that since the outer barrel member 14 which is locked to the hub 56 of the stylet 22, is pulled rearwardly by a distance equal to the distance the cannula driver 84 is pulled back, the tip 23 of the stylet 22 remains within the tip 21 of the cannula 20, the cannula 20 having been moved proximally into the inner barrel member 12 from its outwardly advanced, at rest position by movement of the cannula driver 84 proximally within the inner barrel member 12.

In such condition of the instrument 10, relative movement between the inner and outer barrel members 12 and 14 can continue, with the position of the cannula driver 84 within the inner barrel member 12 now being "locked" by the latching means 32 and the cannula driver 84 can now be considered "armed", for quickly returning the cannula 20 distally to its at-rest position as described hereinafter.

FIG. 4 is a radial cross-sectional view through the instrument 10 and shows the longitudinal alignment of components when the instrument is armed as shown in FIG. 3.

Turning now to FIG. 5, the user of the instrument 10 then returns the outer barrel member 14 to it former position, moving it distally over the inner barrel member 12 until the point 35 of the trigger 30 is again positioned within the cutout 36 at the proximal end of the latching indicator means 34. Upon such forward or distal movement of the outer barrel member 14 over the inner barrel member 12, since the hub 56 of the stylet 22 is secured to the outer barrel member 14 as will be described below, the stylet 22 is also advanced distally out of the cannula 20, exposing the sampling notch 50 on the stylet 22.

Tissue surrounding the stylet 22 now falls into the exposed notch 50 of the stylet 22 and the user is ready to slice off the bit of tissue within the notch 50 from the surrounding tissue by use of the pointed tip 23 of the cannula 20 which will be quickly advanced distally over the stylet 22 and will act as a cutting edge for the instrument 10.

Turning now to FIG. 6, to accomplish such dissection of the tissue which has fallen into the notch 50, the user actuates the trigger 30 of the instrument 10 by depressing the proximal end portion 40 of the trigger 30. The point 35 of the trigger 30 is moved downwardly through the cutout 36 in the outer barrel member 14, and into the cutout 76 in the inner barrel member 12, which is aligned directly beneath the cutout 36 in the outer barrel member 14 when the outer barrel member 14 is in its most distal at-rest position over the inner barrel member 12, and contacts the distal end portion 104 of the flap 100 which, as shown in FIG. 3, is biased against the distal end wall 112 of the cutout 76 of the inner barrel member 12. A continued downward force on the trigger 30 will force the distal end portion 104 of the flap 100 downwardly, and the vertical distal end wall 106 of the flap 100 is eventually released from its abutment against the distal wall 112 of the cutout 76. This disengagement of the flap 100 releases the latching means 32 and thus spring 94 from its locked, extended condition and allows the spring 94 to quickly contract to its compressed, at-rest condition. Such contraction of the spring 94 pulls distally on the first stepped portion 86 of the cannula driver 84 to which the spring 94 is attached and the cannula driver 84 rapidly advances the cannula distally over the tissue within the notch 50 and the user hears a "snap" produced by the second stepped section 92 of the cannula driver 84 hitting the second stepped section 90 of the plug 18, confirming distal movement of the cannula 20 over the stylet 22. The trigger 30 upon release of the downward force thereon also returns quickly to its at-rest position.

Once the cannula 20 has been advanced quickly or "shot" over the stylet 22, it entraps a sheared tissue specimen within the specimen notch 50 and the instrument 10 is returned to its original at-rest condition, as shown in FIG. 7. As illustrated, the trigger 30 is again positioned within the cutout 36 in the outer barrel member 14, the cutout 36 in the inner barrel member 12 is again aligned directly under the cutout 76 in the outer barrel member 14, and the flap 100 of the cannula driver 84 once again is inwardly displaced, with the end edge 108 of the distal wall 106 resting lightly against the inner barrel member 12.

It is preferable, in any core biopsy instrument 10, to be able to remove the stylet 22 from the proximal end 42 of the instrument 10 without dislodging the cannula 20 from a particular position within a patient. A user may, for example, want to make sure that the tissue sample is adequate in size, or is from the correct location, prior to dislodging the entire instrument 10 from within the body of the patient. For this reason, as illustrated in FIGS. 8 and 9, the instrument 10 of the present invention is provided with a proximally removable stylet 22.

As illustrated in FIG. 8, which is a cross sectional top plan view into the instrument 10, the stylet hub 56 has two laterally outwardly biased legs 114 and 116 which extend proximally from a bullet shaped distal end portion 118 of the hub 56. The legs 114 and 116 terminate proximally of the proximal end 42 of the outer barrel member 14. Each leg has one of the wings 46 extending laterally outwardly therefrom along the proximal end 42 of the flange 44 of the outer barrel member 14 and each wing 46 has the serrated proximal end face 47. These wings 46 can be moved toward each other, as illustrated in FIG. 9, to release a laterally outwardly extending rib 120 of each leg 114, 116 from entrapment between the peripheral rib 64 and two proximal inwardly extending flanges 122 which form an inward continuation of the rear flange 44 of the outer barrel member 14.

As shown in FIG. 9, when the wings 46 are pinched together, the ribs 120 are disengaged from entrapment between the peripheral rib 64 and the flanges 122 of the outer barrel member 14 and the stylet 22 can be removed from the proximal end 42 of the instrument 10 by pulling proximally on the stylet hub 56 until the stylet 22 exits the proximal end 42 of the instrument 10.

Likewise, if the stylet 22 must be reinserted, such as for obtaining a further sample, or obtaining a sample from a slightly different position, the user merely slides the stylet 22 and hub 56 therefor back into the instrument 10 until it "clicks" into engagement with the outer barrel member 14 as defined above, and the instrument 10 is ready to be used again.

In FIG. 10, the simplicity of the instrument 10 is illustrated in an exploded perspective view of the components of the instrument 10. As shown, the instrument 10 is comprised of four major components or sections; the outer barrel member 14; the inner barrel member 12 which is slidably received within the outer barrel 14; the cannula driver 84 including the cannula 20 which is slidably received within and extends distally outwardly of the inner barrel member 12; and the hub 56 mounting the stylet 22 which extends through the length of the instrument 10.

The instrument 10 is disposable and may be made of any suitable hard polymer, such as ABS. The cannula 20 and stylet 22, of course, are made of stainless steel. Also, although the barrel members 12 and 14 are illustrated as being somewhat polygonal in cross-section, this is not to be considered at all limiting.

The soft tissue core biopsy instrument 10 of the present invention has a number of advantages, some of which have been described above, and others of which are inherent in the invention. Also, modifications can be made to the instrument 10 without departing from the teachings of the present invention. For example, alignment means, which co-act between the hub 56 for the stylet 22 and the proximal end 42 of the outer barrel member 14, to ensure that the sampling notch 50 of the stylet 22 is properly oriented within the instrument 10, can be provided. Accordingly the scope of the invention is only to be limited as necessitated by the accompanying claims.

I claim:

1. A soft tissue core biopsy instrument comprising: a proximal outer barrel member having a distal end and a proximal end;
    a distal inner barrel member which is slidably received within said outer barrel member, which has a distal end and a proximal end and which has a stop in said distal end;
    a cannula driver in said inner barrel member;
    a cannula extending distally from said inner barrel member, being fixed to said cannula driver, and having a distal tip, said cannula driver being slidably received in and movable within said inner barrel member and said cannula extending a predetermined distance out of a distal end of said inner barrel member when the instrument is in ann at-rest condition;
    a stylet having a distal end, a proximal end, and being removably received in said outer barrel, in said inner barrel, and in said cannula, said distal end having a biopsy sample receiving notch therein;
    a stylet hub mounted to said proximal end of said stylet;
    said stylet hub being removably attached to the proximal end of said proximal outer barrel member to enable multiple biopsies to be obtained with one insertion of said cannula, said stylet extending distally from said hub and within said cannula and having a distal tip portion (a) positioned within said cannula when the instrument is in an at-rest position and (b) extending distally of said distal tip of said cannula in position to capture a biopsy sample when the instrument is in a cocked condition;
    biasing means within said inner barrel member between said stop and said cannula driver for biasing said cannula driver;
    latching means associated with said cannula driver and said inner barrel member for latching said cannula driver in a proximally retracted cocked position within said outer barrel member and said inner barrel member against the biasing action of said biasing means;
    and a trigger, associated with said latching means, for unlatching said latching means, said trigger, upon being actuated for unlatching of said latching means, allowing said biasing means to quickly return said cannula driver and said cannula to said distally extending position thereof and over said stylet distal tip portion.

2. The instrument of claim 1 further including latching indicator means on said proximal outer barrel member for indicating when said trigger is latched.

3. The instrument of claim 2 wherein said trigger is an elongate member which extends outwardly from and the proximally generally parallel to said inner barrel member to a free end, said free end having a detent which extends therefrom toward said stylet in said instrument and which rides on and along an outer surface of said proximal outer barrel member within a longitudinal slot in said outer barrel member which defines part of said latching indicator means.

4. The instrument of claim 1 wherein said trigger is mounted to said inner barrel member and extends distally over said outer barrel member.

5. The instrument of claim 1 wherein said inner barrel member has at lest one lateral longitudinal slot and said cannula driver has a slot therein adapted to be aligned with said longitudinal slot, and said instrument includes at least one pin slidably received in said aligned slots.

6. The instrument of claim 5 wherein said inner barrel member has an opening extending through a sidewall thereof and said cannula driver has a flap cut thereinto, said flap having a free end with a detent thereon extending laterally outwardly therefrom and being aligned with said opening in said inner barrel member when said outer barrel member is pulled proximally, pulling said cannula driver proximally therewith by means of engagement of said at least one pin in said aligned slots, said flap and said opening forming said latching means for the instrument for holding said cannula driver proximally against the acting of said biasing means.

7. The instrument of claim 6 wherein said opening in said inner barrel member is aligned directly beneath an opening in the sidewall of said proximal outer barrel member which opens into said longitudinal slot defining part of said latching indicator means on said outer barrel member and wherein said detent of said trigger rests in said opening in said outer barrel member when said outer barrel member is at its most proximal, at-rest position, over said inner barrel member.

8. The instrument of claim 1 wherein said inner barrel member includes a distal nose plug that has a proximal end which extends into the inner barrel member and which includes first and second inwardly stepped portions, wherein a distal end of said cannula driver includes first and second inwardly stepped portions, and wherein said biopsy means extends between said proximal end of said nose plug and said distal end of said cannula driver.

9. The instrument of claim 8 wherein said second inwardly stepped portion of said cannula driver abuts against said second inwardly stepped portion of said plug when the instrument is in an at-rest condition.

10. The instrument of claim 8 wherein said first inwardly stepped portions of said cannula driver and of said plug, respectively, are threaded and are separated from one another by said second inwardly stepped portions of said plug and said cannula driver.

11. The instrument of claim 7 wherein said biasing means comprise a spring which is threadedly received over and fixed, at one end thereof, to said first inwardly stepped portion of said plug and at the other end thereof to said first inwardly stepped portion of said cannula driver, said spring being contracted when the instrument is in an at-rest condition.

12. The instrument of claim 11 wherein said second inwardly stepped portions of said cannula driver and of said plug are received within central coils of said spring and are movable within said coils.

13. The instrument of claim 1 wherein said proximal outer barrel member has a proximal end wall with an aperture therein through which said stylet hub extends, said stylet hub is longitudinally bifurcated at its proximal end to provide two proximally extending flexible legs, each leg having a laterally outwardly extending rib which coacts with a portion of said end wall of said proximal outer barrel member adjacent said aperture for holding said stylet in said instrument.

14. The instrument of claim 13 wherein said legs of said hub also have laterally outwardly extending wings which can be flexed inwardly toward one another to flex said legs inwardly and release said ribs from their positions adjacent said end wall of and within said proximal outer barrel member to allow said stylet hub to be withdrawn proximally from within said proximal outer barrel member.

15. The instrument of claim 13 including alignment means on said stylet hub and in said proximal outer barrel member which coact to align the rotational position of the stylet mounted on said stylet hub relative to the rotational position of said cannula so that pointed ends of said stylet and said cannula are rotationally oppositely disposed.

16. The instrument of claim 1 wherein a pin extends through aligned openings in the walls of said inner barrel member, of said outer barrel member and of said cannula driver to maintain said barrel members and said cannula driver slidably united.

* * * * *

UNITED STATES PATENT AND TRADEMARK OFFICE
CERTIFICATE OF CORRECTION

PATENT NO. : 4,881,551
DATED : November 21, 1989
INVENTOR(S) : Glenn N. Taylor

It is certified that error appears in the above-identified patent and that said Letters Patent is hereby corrected as shown below:

Column 3, line 32 "tipportion" should be --tip portion--.

Column 9, line 51 "ann" should be --an--.

Column 10, line 48 "acting" should be --action--.

Abstract, line 20 "biposies" should be --biopsies--.

Signed and Sealed this

Second Day of March, 1993

Attest:

STEPHEN G. KUNIN

Attesting Officer

Acting Commissioner of Patents and Trademarks